United States Patent [19]

Wöhner et al.

[11] Patent Number: 4,828,998
[45] Date of Patent: May 9, 1989

[54] BACTERIOLYTIC ENZYME PRODUCT FROM STREPTOMYCES, A PROCESS FOR ITS PREPARATION, AND A STRAIN SUITABLE FOR THIS PURPOSE

[75] Inventors: Gerhard Wöhner, Flörsheim am Main; Hartmut Voelskow, Hattersheim am Main; Paul Präve, Sulzbach; Erich Lück, Bad Soden am Taunus; Gert-Wolfhard von Rymon Lipinski, Frankfurt am Main, all of Fed. Rep. of Germany

[73] Assignee: Hoechst Aktiengesellschaft, Fed. Rep. of Germany

[21] Appl. No.: 795,543

[22] Filed: Nov. 6, 1985

[30] Foreign Application Priority Data

Nov. 8, 1984 [DE] Fed. Rep. of Germany ....... 3440735

[51] Int. Cl.$^4$ .......................... C12N 9/36; C12N 1/20; C12N 1/06; C12R 1/465
[52] U.S. Cl. .................................. 435/206; 435/886; 435/259; 435/253.5
[58] Field of Search ............... 435/206, 253, 886, 200, 435/259

[56] References Cited

U.S. PATENT DOCUMENTS

| | | | |
|---|---|---|---|
| 3,816,259 | 6/1974 | Collinge et al. | 435/207 |
| 3,816,260 | 6/1974 | Sugiyama | 435/206 |
| 3,868,303 | 2/1975 | Tsumura et al. | 435/206 |
| 3,929,579 | 12/1975 | Yoshimura et al. | 435/206 |
| 3,969,189 | 7/1976 | Kobayashi et al. | 435/206 |
| 4,532,208 | 7/1985 | Hafner et al. | 435/94 |

FOREIGN PATENT DOCUMENTS 1248896 10/1971 United Kingdom .
1369874 10/1974 United Kingdom .

OTHER PUBLICATIONS

ATCC Catalogue of Bacteria, 16th Edition 1985 p. 181.

Primary Examiner—Thomas G. Wiseman
Assistant Examiner—Charles L. Patterson, Jr.
Attorney, Agent, or Firm—Finnegan, Henderson, Farabow, Garrett & Dunner

[57] ABSTRACT

The strain *Streptomyces coelicolor* DSM 3030 excretes into the fermentation medium high yields of a bacteriolytic enzyme product which is very active against Gram-positive and Gram-negative bacteria. Preferred fermentation media contain sugar beet molasses and/or calcium ions.

7 Claims, No Drawings

BACTERIOLYTIC ENZYME PRODUCT FROM STREPTOMYCES, A PROCESS FOR ITS PREPARATION, AND A STRAIN SUITABLE FOR THIS PURPOSE

The production of a bacteriolytic enzyme product by streptomyces has been disclosed and had been described in, for example, German Offenlegungsschriften Nos. 2,011,935, 2,040,440 and 2,146,597. The known processes are, especially with regard to the yield of bacteriolytic enzyme product, very expensive.

The formation of a bacteriolytic enzyme product by streptomyces of the species coelicolor has not hitherto been disclosed. Our own investigations, for example on the type strain DSM 40 233, produced no results. It has now been found, surprisingly, that a very active bacteriolytic enzyme product is produced in high yield by one strain of the species Streptomyces coelicolor. This strain has been deposited at the DSM—the German Collection of Microorganisms—under the number DSM 3030. The invention relates to this strain and to those of its mutants and variants which form a bacteriolytic enzyme product. Other aspects of the invention and preferred embodiments are represented below or set out in the patent claims.

The strain according to the invention was isolated from soil samples. The selection feature was the excretion of an enzyme product which is able to lyse bacteria at pH 3 to 7.

The strain according to the invention grows in customary culture media, into which it releases the bacteriolytic enzyme product. After removal of the cells, the bacteriolytic enzyme product remains in the culture supernatant, from which it can be isolated by conventional methods of protein enrichment and purification, such as alcohol precipitation, ion exchange chromatography, ultrafiltration and gel filtration.

One advantage of the preparation according to the invention of the bacteriolytic enzyme product may be regarded as being the possibility of achieving high yields of bacteriolytic enzyme product in culture media of simple composition. Addition of sugar beet molasses in an amount of 5 to 50 g, preferably 10 to 20 g, per liter of culture medium has proved particularly useful.

A further increase in the yield is achieved by addition to the culture medium of calcium ions in the form of readily soluble, non-toxic calcium salts, preferably in the form of low-cost calcium chloride. A concentration of calcium ions of 0.05 to 1 molar is advantageous, and concentrations of 100 to 500 mmole are particularly preferred, for example in the form of addition of 0.2 to 0.5% by weight of calcium chloride dihydrate.

The bacteriolytic enzyme product which is obtained according to the invention is stable and active in a pH range from below 3 to above 9. At least 80% of the maximal activity in the pH range 3 to 9 was still retained after 16 hours' incubation in buffer mixtures at room temperature.

The temperature optimum for the activity of the bacteriolytic enzyme product is in the range 50° to 60° C. At least 90% of the maximal activity is attained over this range. Starting at a low temperature there is a slow increase in activity with increasing temperatures up to 60° C.: it is about 10% of the maximal activity at room temperature, about 30% at 30° C., and about 60% at 40° C. At higher temperatures there is a rapid decrease in activity: it is about 30% of the maximal activity at 65° C., and it is 10% at 70° C.

The pH otimum for the action of the bacteriolytic enzyme product is 4.5 to 5; the activity is at least 80% in the pH range from about 4.25 to 5.5. There is still about 65% of the maximal activity at pH 4, 25% at pH 3.5, about 75% at pH 5.7 and about 40% at pH 6.

The action of the bacteriolytic enzyme product according to the invention is very good against Gram-positive and Gram-negative bacteria. For this reason, it can (like commercially available lysozymes) be used for preservation of foodstuffs, to prevent infections, and for the preparation of protoplasts.

The invention is illustrated in detail in the examples which follow. Unless otherwise stated, percentage data relate to weight.

EXAMPLE 1

Cultivation of *S. coelicolor*

Slant agar medium which contained 2% soybean meal, 2% mannitol and 1.5% agar (pH 7.5) was inoculated with Streptomyces coelicolor DSM 3030 and cultivated at 30° C. for 10 days. 10 ml of a sterile solution of 0.9% NaCl and 0.01% of a non-ionic surfactant were added to the slant culture, and the spores were floated off. 0.2 ml of the spore suspension was used as inoculum for shake cultures of 100 ml of culture medium in 300 ml-capacity culture flasks.

The culture media nos. 1–3 listed in table 1 were made up, inoculated and shaken at a rate of 160 rpm at 30° C. Samples were taken after 2, 4 and 6 days, the cells were spun down, and the activity of the bacteriolytic enzyme product in the culture supernatant was determined (Table 2).

The highest yield of bacteriolytic enzyme product was obtained with nutrient solution 3 which contained 2% sugar beet molasses in addition to glucose, soybean meal and casein peptone.

TABLE 1

| | Culture media | | |
| | | Medium No. | |
| % | 1 | 2 | 3 |
|---|---|---|---|
| Glucose | 2 | | 1 |
| Mannitol | | 2 | |
| Soybean meal | 2 | 1 | 0.5 |
| Casein peptone | | | 0.5 |
| Molasses | | 1 | 2 |

TABLE 2

| Activity of bacteriolytic enzyme product in the culture supernatant (U/ml) | | | |
|---|---|---|---|
| Fermentation time | | Medium No. | |
| Days | 1 | 2 | 3 |
| 2 | 21 | 15 | 363 |
| 4 | 367 | 378 | 1106 |
| 6 | 236 | 558 | 2088 |

EXAMPLE 2

Increasing the yield by addition of calcium

*Streptomyces coelicolor* DSM 3030 was cultivated in the manner described in Example 1, on a nutrient medium which contained 1% glucose, 2% molasses, 0.5% soybean meal, 0.5% casein peptone and 0.5% $CaCl_2 \times 2$-$H_2O$. A considerable increase in the yield of bacteriolytic enzyme product to 768 U/ml, 2462 U/ml and 4715

U/ml in the culture supernatant after 2, 4 and 6 days was obtained by the addition of $CaCl_2$.

EXAMPLE 3

Fermentation 10 ml of a suspension of *Streptomyces coelicolor* DSM 3030 spores according to 5 l of culture medium in an 8 l fermenter.

| Fermentation conditions: | |
|---|---|
| Culture medium: | 1% glucose |
| | 2% molasses |
| | 0.5% soybean meal |
| | 0.5% casein peptone |
| | 0.2% $CaCl_2 \times 2H_2O$ |
| pH: | 6.3 |
| Temperature: | 33° C. |
| Stirrer speed: | 300 rpm |
| Air input: | 3 l/min |

After the fermentation had lasted 4 days, the sucrose concentration (from the molasses) had decreased to about zero. The cells were removed by centrifugation, and the bacteriolytic enzyme product was isolated from the culture supernatant by alcohol precipitation, ion exchange chromatography, ultrafiltration and gel filtration.

In Table 3 which follows, the activity of the bacteriolytic enzyme product found in the culture supernatant has been set equal to 100% yield. The percentages given in the column "yield" thus relate to that proportion recovered with the isolation method stated in the first column.

The meanings of the symbols in the column "method" are:

0 = no isolation (activity in the culture supernatant)
1 = ethanol precipitation and dissolution of the precipitate in buffer
2 = cation exchange chromatography
3 = ultrafiltration
4 = gel filtration.

Determination of the activity of bacteriolytic enzyme product:

0.2 ml samples containing bacteriolytic enzyme product are pipetted into 2.8 ml of a suspension of 0.2 mg of Micrococcus luteus ATCC 4698 (Boehringer Mannheim) per ml of 0.1 sodium acetate buffer (pH 5.0), and the decrease in turbidity was determined at 25° C. by measurement of the extinction at 450 nm. 1 U is defined as a decrease in extinction of 0.001 per minute.

Protein determination:

Method of Lowry, Rosebrough, Farr and Randall, J. Biol. Chem. 193, 265 (1951).

EXAMPLE 4

Lytic activity

The microorganisms specified in Table 4 are cultivated for 24 hours, and the cells are spun down (5 minutes at 1500 g), washed $2 \times 0.1$ N sodium acetate buffer (pH 5.0) and are thoroughly suspended in this acetate buffer. The abovementioned determination of the activity of bacteriolytic enzyme product is carried out in this suspension. Table 4a lists Gram-positive, and Table 4b lists Gram-negative, bacteria. Egg lysozyme is used as reference in each instance.

TABLE 3

| | | Isolation of the bacteriolytic enzyme product | | | | |
|---|---|---|---|---|---|---|
| | Processed quantity of | Enzyme activity | | Amount of protein in | | |
| Process | culture supernatant [ml] | [U/ml] | [U/processed · $10^6$ quantity] | processed quantity [mg/ml] | Specific activity [U/mg Protein] | Yield [%] |
| 0 | 4,400 | 10,800 | 47.5 | 5.84 | 1,850 | 100 |
| 1 | 120 | 376,100 | 45.1 | 134.3 | 2,800 | 94.9 |
| 2 | 210 | 200,470 | 42.1 | 14.4 | 13,922 | 88.6 |
| 3 | 60 | 685,000 | 41.1 | 43.3 | 15,820 | 86.5 |
| 4 | 180 | 212,300 | 38.2 | 10.2 | 20,814 | 80.4 |

TABLE 4a

| | | DSM 3030 bacteriolytic enzyme product % lysis after: | | Egg lysozyme % lysis after: | |
|---|---|---|---|---|---|
| Collection No. | Microorganisms | 30 min | 15 h | 30 min | 15 h |
| ATCC 10240 | Micrococcus flavus | 6.3 | 64.0 | 42.1 | 79.2 |
| | Micrococcus pyogenes | 29.8 | 53.0 | 11.4 | 41.5 |
| ATCC 6538 | Staphylococcus aureus | 0 | 21.7 | 2.1 | 18.3 |
| ATCC 10541 | Streptococcus faecalis | 8.8 | 44.2 | 0.5 | 11.9 |
| DSM 20200 | Leuconostoc cremoris | 16.1 | 73.1 | 1.8 | 11.8 |
| DSM 20193 | Leuconostoc mesenteroides | 16.6 | 46.0 | 0 | 7.7 |
| ATCC 9341 | Sarcina lutea | 0 | 17.5 | 1.2 | 15.0 |
| ATCC 9341 a | Sarcina lutea | 1.2 | 11.0 | 2.0 | 18.8 |
| ATCC 11778 | Bacillus cereus | 4.8 | 38.8 | 4.9 | 23.5 |
| ATCC 13732 | Clostridium butyricum | 0 | 34.3 | 0 | 0 |
| | Clostridium tyrobutyricum | 2.8 | 25.5 | 0 | 0 |
| | Clostridium pectinovorum | 21.2 | 69.4 | 8.2 | 27.0 |
| | Clostridium acetobutylicum | 0 | 47.3 | 0 | 0 |
| ATCC 11443 | Lactobacillus casei | 1.6 | 17.1 | 0 | 6.6 |
| ATCC 4963 | Lactobacillus acidophilus | 4.9 | 38.3 | 0 | 4.8 |
| DSM 2129 | Lactobacillus bulgaricus | 3.6 | 54.0 | 5.9 | 28.6 |
| ATCC 6946 | Corynebacterium simplex | 8.6 | 70.9 | 4.4 | 28.1 |
| ATCC 7005 | Corynebacterium hoagii | 4.6 | 46.2 | 4.0 | 34.7 |
| NCJB 9114 | Streptomyces aureofaciens | 33.8 | 55.4 | 18.7 | 41.4 |
| NRRL 3585 | Streptomyces clavuligerus | 44.4 | 90.1 | 12.9 | 35.7 |
| NRRL 8057 | Streptomyces cattleya | 41.9 | 65.2 | 19.8 | 57.6 |
| ATCC 21317 | Arthrobacter paraffineus | 10.3 | 25.9 | 2.9 | 19.3 |

TABLE 4a-continued

| Collection No. | Microorganisms | DSM 3030 bacteriolytic enzyme product % lysis after: | | Egg lysozyme % lysis after: | |
|---|---|---|---|---|---|
| | | 30 min | 15 h | 30 min | 15 h |
| | Mycobacterium 607 | 12.0 | 27.5 | 18.9 | 27.0 |

TABLE 4b

| Collection No. | Microorganisms | DSM 3030 bacteriolytic enzyme product % lysis after: | | Egg lysozyme % lysis after: | |
|---|---|---|---|---|---|
| | | 30 min | 15 h | 30 min | 15 h |
| ATCC 14909 | Pseudomonas alcaligenes | 39.6 | 56.9 | 15.4 | 33.0 |
| ATCC 13985 | Pseudomonas aureofaciens | 7.0 | 18.5 | 0 | 0 |
| ATCC 13525 | Pseudomonas fluorescens | 5.9 | 9.8 | 0 | 1.7 |
| ATCC 11172 | Pseudomonas fluorescens | 3.6 | 55.8 | 0 | 20.8 |
| ATCC 4973 | Pseudomonas fragi | 3.3 | 18.4 | 0 | 0 |
| ATCC 12099 | Pseudomonas rubescens | 5.3 | 13.1 | 0 | 0 |
| | Xanthomonas spec. | 3.4 | 8.3 | 2.2 | 5.1 |
| ATCC 11105 | Escherichia coli | 2.4 | 8.1 | 0.6 | 3.7 |
| | Escherichia coli | 45.6 | 61.9 | 14.0 | 22.2 |
| | Escherichia coli | 44.4 | 86.0 | 7.8 | 21.1 |
| | Escherichia coli | 50.2 | 77.3 | 17.0 | 23.5 |
| | Klebsiella pneumoniae | 43.9 | 72.5 | 28.7 | 47.4 |
| | Klebsiella pneumoniae | 34.2 | 16.7 | 1.1 | 2.1 |
| | Enterobacter spec. | 6.2 | 37.9 | 0.5 | 30.3 |
| | Aerobacter vinelandii | 17.5 | 42.9 | 8.0 | 7.6 |
| | Serratia marcescens | 5.3 | 15.2 | 0.6 | 2.3 |
| NRRL-B-3874 | Flavobacterium spec. | 3.5 | 33.6 | 0 | 11.5 |
| NRRL-B-5641 | Flavobacterium spec. | 2.4 | 27.5 | 0.8 | 10.9 |
| | Flavobacterium dehydrogen. | 18.2 | 37.3 | 2.9 | 7.6 |
| ATCC 31062 | Flavobacterium spec. | 2.5 | 23.9 | 2.4 | 15.8 |

EXAMPLE 5

Lytic activity in milk

As an assay system relating to practice, 9 ml of pasteurized whole milk and 1 ml of a solution containing 400 U of the bacteriolytic enzyme product were added to 1 ml of 24-hour old cultures of the bacteria specified in Table 5 and samples were taken immediately, after 1 hour and after 20 hours, and the live bacteria counts in these were determined. For the reference value, 1 ml of sterile water is introduced into the assay system in place of the solution containing the bacteriolytic enzyme product.

COMPARISON EXAMPLE

The yield of the bacteriolytic enzyme product from the strain DSM 3030 was compared with that of S. globisporium ATCC 21553 which is mentioned in German Offenlegungsschrift No. 2,146,597. In Table 6 "Medium B" means the liquid medium specified in "Reference Example 1" of German Offenlegungsschrift No. 2,146,597 (Canadian Patent No. 958,339):

TABLE 6

| Medium | Strain | Enzyme activity in the culture supernatant after ... days in U/ml | | | | | | |
|---|---|---|---|---|---|---|---|---|
| | | 2 | 3 | 4 | 5 | 6 | 7 | 8 |
| A | DSM 3030 | 253 | 788 | 2036 | 3478 | 4130 | 5605 | 6600 |
| | ATCC 21553 | 0 | 0 | 98 | 308 | 596 | 683 | 643 |
| B | DSM 3030 | 0 | 0 | 290 | 1250 | 1664 | 2068 | 2280 |
| | ATCC 21553 | 0 | 0 | 276 | 859 | 1130 | 1171 | 1247 |

TABLE 5

| Gram | Bacteria | Determination of bacteria count after | No lysozyme (reference value) Bacteria/ml × $10^5$ | DSM 3030 bacteriolytic enzyme product Bacteria/ml × $10^5$ | Egg lysozyme Bacteria/ml × $10^5$ |
|---|---|---|---|---|---|
| + | Corynebacterium simplex | 1 h | 7,700 | 3,900 | 2,400 |
| | ATCC 6946 | 20 h | 33,000 | 3.5 | 120 |
| + | Bacillus subtilis | 1 h | 560 | 450 | 550 |
| | | 20 h | 950 | 530 | 840 |
| + | Lactobacillus casei | 1 h | 200 | 210 | 290 |
| | ATCC 11443 | 20 h | 1,300 | 1,500 | 2,000 |
| + | Clostridium pectinovorum | 1 h | 460 | 210 | 580 |
| | | 20 h | 1,200 | 140 | 300 |
| − | Escherichia coli | 1 h | 5.1 | 42 | 38 |
| | | 20 h | 340 | 20 | 23 |
| − | Escherichia coli | 1 h | 36 | 28 | 40 |
| | | 20 h | 2,400 | 16 | 82 |
| − | Klebsiella pneumoniae | 1 h | 700 | 580 | 770 |

TABLE 5-continued

| Gram | Bacteria | Determination of bacteria count after | No lysozyme (reference value) Bacteria/ml × $10^5$ | DSM 3030 bacteriolytic enzyme product Bacteria/ml × $10^5$ | Egg lysozyme Bacteria/ml × $10^5$ |
|---|---|---|---|---|---|
| − | Serratia marcescens | 20 h | 1,100 | 550 | 130 |
| | | 1 h | 360 | 50 | 55 |
| | | 20 h | — | — | — |

We claim:

1. A bacteriolytic enzyme product obtained by fermentation of *Streptomyces coelicolor* DSM 3030, characterized as having a pH optimum of 4.5 to 5.0, temperature optimum of 50° to 60° C. and the ability to lyse bacteria at a pH of 3.0 to 9.0.

2. The bacteriolytic enzyme product as claimed in claim 1, further characterized by attaining at least 90% of its maximal activity at the temperature optimum range.

3. A biologically pure culture of *Streptomyces coelicolor* DSM 3030 and those of its mutants and variants which form the bacteriolytic enzyme product as claimed in claim 1.

4. A process for the preparation of a bacteriolytic enzyme product, which comprises cultivating the strain *Streptomyces coelicolor* DSM 3030 until a significant amount of said bacteriolytic enzyme product is accumulated in the fermentation medium.

5. The process as claimed in claim 4, wherein the fermentation medium contains sugar beet molasses.

6. The process as claimed in claim 4, wherein the fermentation medium contains calcium ions.

7. The process as claimed in claim 5, wherein the fermentation medium contains calcium ions.

* * * * *